United States Patent [19]

Wilson

[11] Patent Number: 4,671,291
[45] Date of Patent: Jun. 9, 1987

[54] ANGLE ENCODING CATHETER

[75] Inventor: David L. Wilson, Edison, N.J.

[73] Assignee: Siemens Medical Systems, Inc., Iselin, N.J.

[21] Appl. No.: 846,658

[22] Filed: Mar. 31, 1986

[51] Int. Cl.$^4$ .............................................. A61M 25/00
[52] U.S. Cl. ................................. 128/658; 604/280
[58] Field of Search ........................... 128/656–658; 604/280–282

[56] References Cited

U.S. PATENT DOCUMENTS 2,212,334  8/1940  Wallerich ........................ 604/280 X
4,279,252  7/1981  Martin ............................ 128/658 X

OTHER PUBLICATIONS

ACMI Catalogue 1960–pp. 34, 35 & 52.

Primary Examiner—Dalton L. Truluck
Attorney, Agent, or Firm—Mark H. Jay

[57] ABSTRACT

A catheter has at least three unevenly spaced radio-opaque bands along its length. By counting the number of bands which are individually identifiable in an arteriogram, the orientation of the catheter can be approximated. This makes it possible to approximate the absolute distances on the arteriogram image.

3 Claims, 6 Drawing Figures

ANGLE ENCODING CATHETER

BACKGROUND OF THE INVENTION

The invention relates to arteriography, and more particularly relates to catheters which are used in arteriography.

Such catheters are used to image arteries by injecting radio-opaque contrast material into the bloodstream. Images of the artery are formed using an X-ray camera.

To maximize the usefulness of arteriograms which are so produced, it is desirable to calibrate the images to determine, e.g. the diameter of an artery or the size of a sterosis in an artery. This presupposes an accurate knowledge of the distance between two points in the image, which distance can then be used as a gauge to calibrate the rest of the image.

It is known to use points along the catheter as such a gauge. This is done by providing two X-ray opaque bands of known spacing from each other. This produces two identifiable points in the image. Where the catheter is parallel to the image intensifier of the X-ray unit, this method works well because the apparent spacing between the points is then an accurate gauge for calibrating the image.

However, the catheter may not be parallel to the image intensifier unit. As a result, the observed distance between the two bands on the catheter image is not an accurate measure by which to calibrate the rest of the image, because the clinician does not know the relative angle between the catheter and the image intensifier and therefore does not know how much shortening of the distance between the bands in the image has taken place.

It would be advantageous to provide a means whereby arteriograms could be accurately calibrated.

One object of the invention is to provide a device which can be used to calibrate catheter arteriograms.

Other objects are to provide a device which makes it possible to calibrate catheter arteriograms in a simple and convenient manner, and in general to improve on known devices used in arteriography.

SUMMARY OF THE INVENTION

In accordance with the invention, there is provided a catheter which has more than two bands which are opaque to radiation. The bands are unevenly spaced. In this way, the apparent distance between adjacent bands in the image indicates the relative angle between the catheter and the image intensifier and thereby provides an approximate correction factor by which the apparent distances can be corrected to derive their true values. This is turn permits the entire image to be calibrated.

In preferred embodiments, there are a relatively large number (such as seven) bands which are arranged in a sequence such that the spacing between adjacent bands increases from one end of the catheter towards the other. This provides a six step resolution of the orientation of the catheter, because as the inclination of the catheter increases, more and more of the adjacent bands will form a continuous opague strip on the image and the number of separately distinguishable bands is therefore indicative of catheter inclination.

Advantageously, each band is approximately 1.2 times the diameter of the catheter. This has the advantage that non-opaque regions caused by X-rays passing through the center of the opaque bands do not appear. This would introduce the possibility of confusion. Additionally, at angles above approximately 50°, the entire banded length of the catheter appears as a single opaque strip.

BRIEF DESCRIPTION OF THE DRAWINGS

Exemplary and non-limiting preferred embodiments of the invention are shown in the drawings, in which.

DETAILED DESCRIPTION OF PREFERRED EMBODIMENTS

Figure 3:
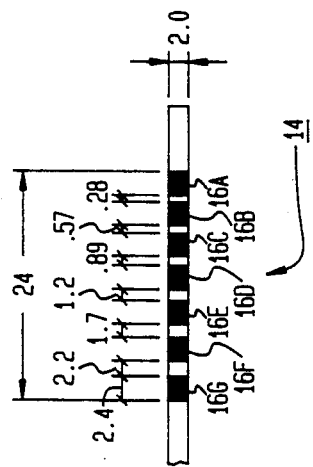
FIG. 3 illustrates a preferred embodiment of the invention.
Figure 1:
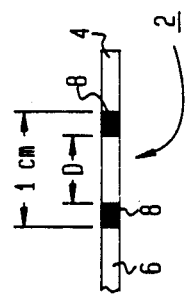
FIG. 1 illustrates a known catheter for use in arteriography.

A conventional catheter 2 such as is used for arteriography has a distal end 4 which is introduced into, e.g. a coronary artery to be examined and a proximal end 6, which is connected to a supply of radiocontrast material (not shown). The catheter 2 is made e.g. of non-rigid polyurethane. Two radio-opaque bands 8 of e.g. tantalum and of known spacing are located on the catheter 2.

An image of the catheter 2 is formed by the image intensifier 10 of an X-ray unit which irradiates the region under investigation, the radiation being directed normal (along direction 12) to the image intensifier 10. Where the catheter 2 is parallel to the image intensifier 10, the distance D between the bands 8 in the image produced by the image intensifier 10 is an accurate measure for calibrating the rest of the image.

Figure 2:
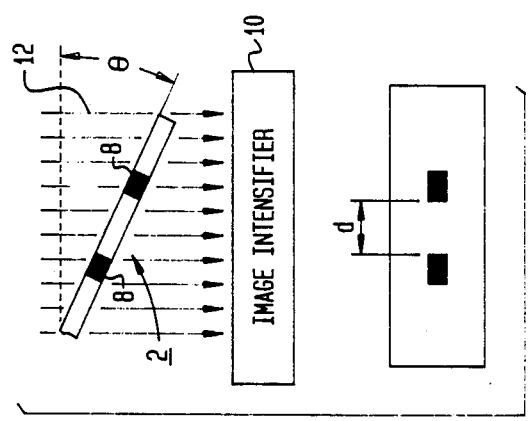
FIG. 2 illustrates foreshortening of the distance between adjacent calibration bands.

Where, as is shown in FIG. 2, the catheter 2 is at an angle O with respect to the image intensifier 10, the distance between the bands 8 is foreshortened in the image. Therefore, the apparent distance d as registered by the image intensifier 10 between the two bands 8 is not an accurate benchmark to use in scaling the absolute size of the image of the artery under investigation. This is because the angle O between the catheter 2 and the image intensifier 10 cannot be conveniently determined in a clinical environment.

The preferred embodiment is constructed (using conventional materials and techniques) so that its angular position with respect to the image intensifier 10 may be approximated merely by examining the image produced by the image intensifier 10. In the preferred embodiment, there are provided on the catheter 14 seven radiation-opaque bands 16A, 16B, ... 16G. These bands 16A ... 16G are arranged in a sequence in which the spacing between each two adjacent bands increases from one end of the catheter 14 to the other; in this example, the interband spacing increases from the distal end towards the proximal end. Advantageously, the spacing between the bands is as follows:

| Spacing | Distance (mm) |
| --- | --- |
| 16A to 16B | 0.28 |
| 16B to 16C | 0.57 |
| 16C to 16D | 0.89 |
| 16D to 16E | 1.2 |
| 16E to 16F | 1.7 |
| 16F to 16G | 2.2 |

Figure 4C:
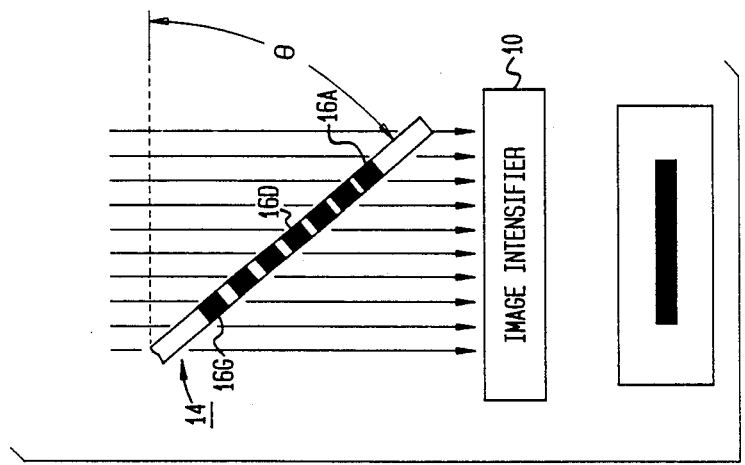
FIGS. 4A, 4B, and 4C illustrate how the preferred embodiment can be used to estimate the angle between itself and an image intensifier.
Figure 4B:
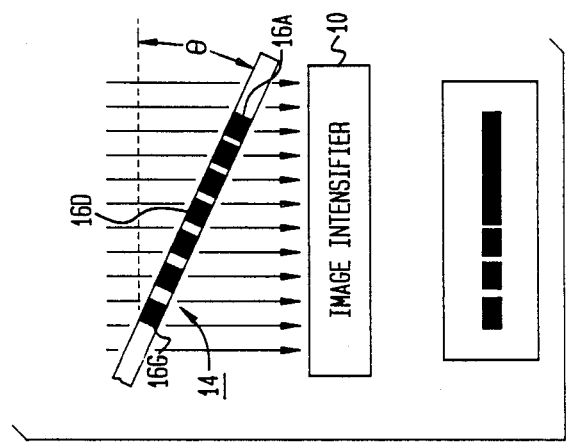
Figure 4A:
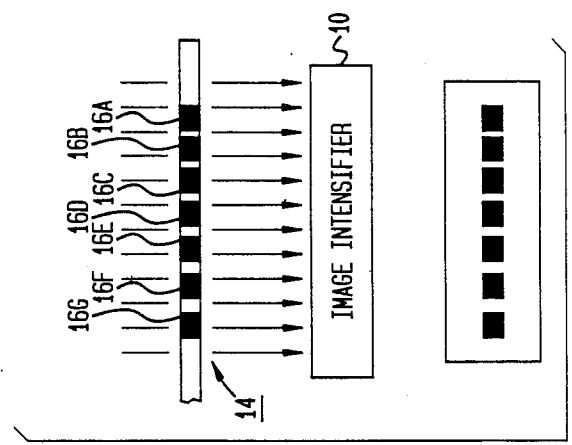

As is shown in FIG. 4, the approximate orientation of the catheter 14 can be determined by a quick examination of the image produced by the image intensifier 10. For angles O between 0° and approximately 8°, the images of the two bands 16A and 16B will be separately distinguishable. At angles between approximately 8° and 16°, the images of bands 16A and 16B will merge, but band 16C will still be separately distinguishable. At approximately 50°, none of the bands 16A . . . 16F can be separately distinguished from any of the others. The approximate angle O can be determined using the following table:

| Number of Gaps | O |
| --- | --- |
| 6 | 0°–8° |
| 5 | 8°–16° |
| 4 | 16°–24° |
| 3 | 24°–32° |
| 2 | 32°–40° |
| 1 | 40°–48° |
| 0 | 48°– |

Thus, by counting the number of gaps between the bands, a clinician can quickly estimate the angle O of the catheter 14 with respect to the image intensifier 10. This permits the amount of foreshortening of any known dimension (for example, the 24 mm distance between the outermost edges of bands 16A and 16G) to be trigonometrically corrected for the inclination of the catheter 14. Thus, enough information is available to permit the image produced by the image intensifier 10 to be scaled to reasonable accuracy.

Advantageously, the bands 16A . . . 16G are approximately 1.2 times as wide as the diameter of the catheter 14; since a number 7 French catheter has a diameter of approximately 2 mm, the bands 16A . . . 16G are approximately 2.4 mm wide. This width is chosen to prevent ambiguous gaps from appearing in the final image at angles of inclination which are less than approximately 50°. These ambiguous gaps would otherwise arise with narrower bands because at such extreme angles, radiation would pass through the center of the bands and this would introduce light regions which could be misinterpreted as gaps between adjacent bands.

Those skilled in the art will understand that changes can be made in the preferred embodiments here described, and that these embodiments can be used for other purposes. Such changes and uses are within the scope of the invention, which is limited only by the claims which follow.

What is claimed is:
1. An angle encoding catheter, comprising:
   a catheter having at least three radiation-opaque bands, the bands being arranged in a sequence such that the separation between each two adjacent bands increases from one end of the catheter to another end thereof.
2. The catheter of claim 1, wherein each of the bands has a width equalling approximately 1.2 times the diameter of the catheter.
3. The catheter of claim 1, wherein there are seven bands.

* * * * *